(12) United States Patent
Lammers et al.

(10) Patent No.: US 9,334,232 B2
(45) Date of Patent: May 10, 2016

(54) PROCESS TO PREPARE A CHELATING AGENT OR PRECURSOR THEREOF USING A CYANIDE SALT

(75) Inventors: Hans Lammers, Arnhem (NL); Martin Heus, Arnhem (NL); Tjerk Oedse Boonstra, Duiven (NL); Adrianus Maria Reichwein, Velp (NL)

(73) Assignee: AKZO NOBEL CHEMICALS INTERNATIONAL B.V., Amersfoort (NL)

(*) Notice: Subject to any disclaimer, the term of this patent is extended or adjusted under 35 U.S.C. 154(b) by 1133 days.

(21) Appl. No.: 13/322,720

(22) PCT Filed: Jun. 3, 2010

(86) PCT No.: PCT/EP2010/057776
§ 371 (c)(1),
(2), (4) Date: Feb. 24, 2012

(87) PCT Pub. No.: WO2010/139755
PCT Pub. Date: Dec. 19, 2010

(65) Prior Publication Data
US 2012/0142964 A1    Jun. 7, 2012

Related U.S. Application Data

(60) Provisional application No. 61/223,189, filed on Jul. 6, 2009, provisional application No. 61/260,600, filed on Nov. 12, 2009.

(30) Foreign Application Priority Data

Jun. 5, 2009  (EP) ..................................... 09162119
Nov. 10, 2009 (EP) ..................................... 09175559

(51) Int. Cl.
*C07C 227/18*   (2006.01)
*C07C 253/30*   (2006.01)
*C07C 253/08*   (2006.01)
*C07C 229/24*   (2006.01)

(52) U.S. Cl.
CPC ............. *C07C 253/08* (2013.01); *C07C 229/24* (2013.01)

(58) Field of Classification Search
CPC .... C07C 229/24; C07C 253/08; C07C 255/25
USPC ........................................... 562/571; 558/352
See application file for complete search history.

(56) References Cited

U.S. PATENT DOCUMENTS 2,855,428 A    10/1958  Singer et al.
4,743,603 A     5/1988  Bulot
6,307,086 B1   10/2001  Rahm et al.
8,399,705 B2 *  3/2013  Boonstra et al. ............. 562/571
2011/0004016 A1  1/2011  Oftring et al.

FOREIGN PATENT DOCUMENTS

| DE | 4211713 A1 | 10/1993 |
| DE | 197936476 A1 | 2/1999 |
| EP | 0 237 239 A2 | 9/1987 |
| EP | 1004571 A1 | 5/2000 |
| JP | 60-136559 A | 7/1985 |
| JP | 62-223193 A | 10/1987 |
| JP | 10-59912 A | 3/1998 |
| WO | WO 01/87827 A1 | 11/2001 |
| WO | WO 2009/024518 A1 | 2/2009 |
| WO | WO 2009/024519 A1 | 2/2009 |
| WO | WO 2009/109544 A1 | 9/2009 |
| WO | WO 2010/139763 A1 | 12/2010 |

OTHER PUBLICATIONS

"The Real Hazards of the Lab" In the Pipeline. [online] Jan. 24, 2009 [retrieved Mar. 18, 2015]. Retrieved from the Internet: <http://pipeline.corante.com/archives/2009/01/23/the_real_hazards_of_the_lab.php#383906>.*
"Strecker Synthesis" Organic Chemistry Portal [online] Aug. 21, 2004 [retrieved Mar. 18, 2015]. Retrieved from the Internet: <http://www.organic-chemistry.org/namedreactions/strecker-synthesis.shtm>.*
English language machine translation of Office Action dated Jun. 11, 2013 for corresponding Japanese Patent Application No. 2012-513624.
English language machine translation of Office Action dated Jul. 2, 2013 for corresponding Chinese Patent Application No. 201080023426.9.
English language machine translation of JP 10-59912 A published Mar. 3, 1998.
International Search Report for International Application No. PCT/EP2010/057776 dated Oct. 6, 2010.
European Search Report for Application No. 09175559 dated May 21, 2010.
DE4211713 A1 English language machine-translation, Oct. 14, 1993.
Shekhter et al, "A New Synthesis 2-Acyl-1,2,3,6,7,11b-Hexahydropyr . . . of Acylglycines," Chem. of Heterocyclic Compounds, 1993, pp. 170-173, vol. 29, No. 2.

* cited by examiner

*Primary Examiner* — Nyeemah A. Grazier
*Assistant Examiner* — Amanda L Aguirre
(74) *Attorney, Agent, or Firm* — Sandra B. Weiss

(57) ABSTRACT

The present invention relates to a process comprising the reaction of a cyanide with an amino acid and an aldehyde, characterized in that the cyanide is a cyanide salt, the amino acid is aspartic acid and/or glutamic acid in the acidic form, and the process is performed under acidic pH by the addition of between 0 and 1 equivalent of an acid based on the amount of aspartic or glutamic acid.

8 Claims, No Drawings

PROCESS TO PREPARE A CHELATING AGENT OR PRECURSOR THEREOF USING A CYANIDE SALT

REFERENCE TO RELATED APPLICATIONS

This application is a national stage filing under 35 U.S.C. §371 of PCT/EP2010/057776, filed Jun. 3, 2010, which claims the benefit of priority to U.S. Provisional Patent Application Nos. 61/223,189 filed Jul. 6, 2009, and 61/260,600, filed Nov. 12, 2009, and European Patent Application Nos. 09162119.3, filed Jun. 5, 2009 and 09175559.5, filed Nov. 10, 2009, the contents of which are each incorporated herein by reference in their entireties.

The present invention relates to a preparation process for a chelating agent (an amino acid polycarboxylate) or a precursor thereof using a cyanide salt. Many syntheses to carboxymethylate an amino acid are known in which hydrogen cyanide is a starting material. However, hydrogen cyanide is a highly toxic chemical and therefore the handling, storage, and transport thereof are extremely risky and preferably to be avoided.

U.S. Pat. No. 2,855,428 discloses a (so-called Singer) process to prepare amine nitriles by reacting formaldehyde and liquid hydrogen cyanide with an amine compound under acidic conditions.

DE 42 11 713 discloses a process to prepare aminodicarboxylic acid-N,N-diacetic acid compounds by reacting aminodicarboxylic acids with formaldehyde and hydrogen cyanide and hydrolyzing the formed amide and nitrile groups by addition of an acid or base to the reaction mixture. It is also disclosed that aminodicarboxylic acid N,N-diacetic acid compounds can be prepared by reaction with formaldehyde and an alkali metal cyanide. It is suggested that both the reaction with the hydrogen cyanide and the reaction with alkali metal cyanide can be performed at a broad pH range of, respectively, 0 to 11 and 3 to 14, however, in Example 1 the reaction is a classic Singer process (using HCN and aspartic acid at an acidic pH) and in the Example 4 the reaction with the alkali metal cyanide is done at an alkaline pH using sodium aspartic acid as a starting material (i.e. a classic Strecker process)

WO 2009/109544 discloses the preparation process of glutamic acid N,N-diacetic acid tetrasodium salt, of high purity, via cyanomethylation and hydrolysis reactions. The method comprises reacting glutamic acid monosodium salt with formaldehyde and then hydrocyanic acid, further reacting with hydrocyanic acid followed by formaldehyde, and hydrolyzing the product using NaOH to give, after work-up, the tetrasodium salt of glutamic acid N,N-diacetic acid.

WO 2009/024518 discloses the preparation process of alkali metal salts of glutamic acid N,N-diacetic acid via cyanomethylation and hydrolysis reactions. Though in general it is indicated that the raw materials may be hydrogen cyanide, formaldehyde, and glutamic acid or a salt thereof, the only explicit disclosure of the process concerns the reaction of glutamic acid monoalkali metal salt with formaldehyde and hydrocyanic acid (i.e. a classic Singer process) and the reaction of monosodium glutamate with sodium cyanide under basic conditions (i.e. a classic Strecker process).

WO 2009/024519 discloses a process to prepare glutamic acid acetic amides using a reaction wherein monosodium glutamate is reacted with formaldehyde and hydrogen cyanide under acidic conditions that will cause the aminonitrile initially formed not to become saponified immediately to give the dicarboxylate, the acetic amide being acquired in an isolatable form instead. It is suggested that the same reaction can be performed using a number of alternative starting materials, amongst which an alkali metal cyanide instead of hydrogen cyanide, as long as the pH is kept in the same acidic range to prevent saponification.

However, in none of the above prior art documents is it acknowledged that it is possible to make amino acid N,N-dicarboxylate chelating agents of amino acids that contain two carboxylic acid functionalities using an alkali metal cyanide without needing to add more acid than a buffering amount and while still being able to perform a Singer-like process.

It has now been found that chelating agents, or their precursor products, based on amino acids having two carboxylic acid functionalities, like aspartic acid and glutamic acid, can also be prepared using a cyanide salt, such as the alkali metal salt of cyanide, instead of hydrogen cyanide and using the amino acid in the acidic form, if a process is used wherein the pH of the reaction mixture is brought to and maintained at a value that is sufficiently low Accordingly, the present invention provides a process comprising the reaction of a cyanide with an amino acid and an aldehyde, characterized in that the cyanide is a cyanide salt, the amino acid is aspartic acid and/or glutamic acid in the acidic form, and the process is performed under acidic pH by the addition of between 0 and 1 equivalent of an acid based on the amount of aspartic and/or glutamic acid.

Using the process of the present invention it is demonstrated that using and storing large amounts of HCN for the synthesis can be avoided. This leads to improved safety. Also, limited (industrial) availability of HCN is no longer a problem. In this respect it should be noted that in many countries HCN may not be transported other than via a suitable pipeline. As an additional benefit, the compounds prepared by the process of the present invention were found to have much lower impurity levels than comparable processes where cyanide salts are used and as a result the yield over glutamic acid or aspartic acid starting material is higher. Surprisingly, in the process of the invention the initial amount of acid is demonstrated to be sufficient to keep the pH of the reaction mixture sufficiently low to make the reaction proceed with a high yield.

In this respect, it should be noted that DE 42 11 713 discloses in Example 4 the reaction of an aminodicarboxylic acid and formaldehyde with NaCN. However, during this reaction hydroxide is formed as a side product, as a result of which the reaction immediately progresses to the hydrolysis step to give the sodium salt of the carboxylic acid and, moreover, as an undesired side effect of the presence of the hydroxide ions a number of side products are formed, namely undesired derivatives or saponification products like nitrilotriacetate (NTA) but also high amounts of glycolate, all of which can be reduced strongly or avoided by the process of the present invention.

The present process involves a reaction mixture to which cyanide salt is added and in which process the cyanide salt reacts with the aspartic acid and/or glutamic acid and an aldehyde while the cyanide salt is acidified. In a preferred embodiment of the process only in situ hydrogen cyanide is present, as under the process conditions the cyanide reacts instantaneously with the aspartic acid and/or glutamic acid and the aldehyde.

In another embodiment the cyanide salt (also referred to as XCN in this specification) can be an alkali metal cyanide. The alkali metal cyanide preferably is sodium or potassium cyanide. The cyanide salt can also be an alkaline earth metal cyanide salt, as long as it is not insoluble in the reaction solution used.

A benefit of the aspartic acid and/or glutamic acid is their ability to maintain the reaction solution in the acidic pH region that is desired for the process of the present invention, thereby obviating the need to add acid other than a minimal amount to make and/or keep the reaction mixture acidic. Or, in other words, when reacting aspartic acid or glutamic acid in the acidic form with an alkali metal cyanide, it is only necessary to add a minimal amount of acid to be certain that the reaction mixture gets and maintains the acidic pH needed to make the reaction proceed with a high yield. Of aspartic acid and glutamic acid, glutamic acid is the preferred amino acid.

In another preferred embodiment the product of the reaction is at least one amino acid nitrile product of glutamic acid or aspartic acid, formaldehyde, and cyanide.

The solution used for the process of the present invention preferably is an aqueous solution; however, other (organic) solvents may be used as well, like protic solvents, such as e.g. methanol, as well as mixtures of two or more solvents. Mixtures of organic solvents and water are useful when one of the reactants is poorly soluble or insoluble in water.

Depending on the selection of the aspartic acid or glutamic acid, the aldehyde, the cyanide, and, in some cases, on the further raw materials and the reaction conditions, several embodiments of the present invention follow, which are discussed in further detail below.

As indicated above, in a preferred embodiment the process of the invention is a "Singer-like" process to give amino acid nitriles in accordance with the equation below (the reaction equation is only meant to illustrate the invention and not to be fully accurate or complete):

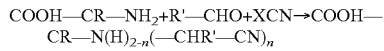

wherein n is 1 or 2, preferably 2, R is an alkyl group containing a carboxylic acid group to give aspartic or glutamic acid, and R' is a carboxylate group, an alkyl group or a hydrogen atom, preferably a hydrogen atom.

The amino acid nitriles formed by this embodiment are suitable precursors in the preparation of chelating agents.

These nitrile compounds can be hydrolyzed to give the corresponding amides or carboxylic acids or the salts thereof that are of use as chelating agents. The hydrolysis is preferably an alkaline hydrolysis.

The pH during the process of the invention is acidic (i.e. between 1 and 7) and in a preferred embodiment is between 3 and 6. While it is possible to suppress polymerization and saponification by controlling other reaction conditions at higher pH ranges, this higher pH at least increases the risk that undesired polymerization reactions of cyanide compounds or saponification reactions will start to occur.

The pH during the process is brought to and/or maintained in the above-mentioned (preferred) range by the addition of an organic or inorganic acid or the use of an acidic ion exchange resin in an amount of more than 0 and less than 1 equivalent on the amount of aspartic and/or glutamic acid.

Preferably, the amount of acid is between 0.1 and 0.8 equivalent, more preferably between 0.1 and 0.6 equivalent.

Suitable organic acids and inorganic acids are selected from hydrochloric acid, hydrobromic acid, hydrofluoric acid, hydroiodic acid, sulfuric acid, nitric acid, phosphoric acid, formic acid, acetic acid, citric acid, lactic acid, malic acid, tartaric acid, maleic acid, or a mixture of two or more of these acids. The acid may also be inherently added in the reaction product of one of the above acids with the amino acid material, like e.g. glutamic acid hydrochloride, or may be an amino acid, or amino polycarboxylic acid.

pH control by adding an organic or inorganic acid may give rise to the formation of inorganic or organic salt containing the cation derived from the cyanide salt used and the anion of the acid used. In a preferred embodiment this disadvantage can be avoided by using one of the products of the process to acidify, like e.g. the organic acid derived from the amino acid nitrile product after it has been converted into the corresponding carboxylate and acidified to a sufficiently low pH to be partly in the form of a carboxylic acid (such as a chelating agent in the acid form, which can be the intended end product of the process, for example glutamic acid, N,N,diacetic acid (GLDA), aspartic acid N,N-diacetic acid (ASDA) or a partial salt thereof of the formula GLDA-NaxHy or ASDA-NaxHy wherein x+y is 4 and y is 2 or more), as the acid to control the pH of the reaction of the cyanide salt with the aspartic acid and/or glutamic acid during reaction.

If another acid is applied, separation of the inorganic or organic salt formed may be needed and this can be conducted using conventional techniques such as crystallization, electrodialysis, ion exchange resins, and membrane filtration (such as nanofiltration).

The process of the invention is generally performed in a semi-batch system in which the cyanide salt solution is added to the aspartic acid and/or glutamic acid and aldehyde with the pH being brought to the predetermined range, and the sample solution is exchanged after completion of each operation. The process can also be performed in continuous operation, for instance by a feed and bleed operation involving continuous addition of the cyanide salt, the aspartic acid and/or glutamic acid, aldehyde, and acid, and removal of the reaction mixture or part of the reaction mixture.

The process of the invention may additionally contain further purification steps. Such purification steps are known to the person skilled in the art and encompass steps like bleaching, stripping, adsorption and absorption treatment, and filtration steps.

EXAMPLES

Example 1

A 1-liter double walled reactor was charged with 147.1 g glutamic acid (1.00 mole) and 450 g of water. To this slurry 326.7 g of a 30% NaCN solution (2.00 moles) and 136.4 g of a 44% formaldehyde solution were added over a period of 4 hrs. 3 hrs after the start of the dosing when the solution was clear, 26 g of acetic acid were added. The temperature of the reaction was 22° C. The pH dropped from 5.2 to 4.7. When the dosing was completed, the reaction mixture was stirred for 30 minutes.

The resulting reaction mixture containing glutamic acid N,N diacetonitrile was saponified by adding it to a boiling solution of 375 g of 30% NaOH over a period of about two hours.

During the saponification the ammonia/water vapour mixture was removed. The reaction temperature was kept at a maximum of 110° C. by adding water. After the dosing was finished, the mixture was boiled for another hour. After cooling, 886.4 g of glutamic acid N,N-dicarboxylate product were collected, with a GLDA-Na4 content of 35.9% (90.6% yield), as determined by a Fe-TSV analysis. The NTA content was well below 0.1 wt % based on the total reaction product.

Comparative Example 2

Preparation of GLDA-Na4 Using a Classic Strecker Synthesis (i.e. Reaction with NaCN Under Basic Conditions)

To a 3-liter reactor 655 g of monosodium glutamate (3.5 moles) and 1,824 g of water were charged under stirring.

Subsequently, 238.8 gr of 50 wt % sodium hydroxide (3.0 moles) were added and next 498.5 g of 34.4 wt % sodium cyanide (3.5 moles) were dosed over 10 minutes. The temperature was increased to 97° C. and 300 g of 35 wt % formaldehyde (3.5 moles) were dosed over about 30 minutes. Subsequently, another 498.5 g of 34.4 wt % sodium cyanide and 300 g formaldehyde were added over about 30 minutes. After the dosing was finished, the temperature was increased to 110° C. over a period of 90 minutes. After cooling, 3185 g of product were collected. The resulting product was analyzed by CZE and $^1$H NMR analysis. The tetrasodium GLDA content was found to be about 8.5% (22% yield). The product was found to contain significant amounts of NTA (about 3.5% on the total reaction mixture, which corresponds to about 40% on the intended GLDA reaction product) and glycolate (about 1.5% on the total reaction mixture, which corresponds to about 15% on the intended GLDA reaction product).

The invention claimed is:

1. A process comprising the reaction of a cyanide with an amino acid and an aldehyde, wherein the cyanide is a cyanide salt, the amino acid is aspartic acid and/or glutamic acid in the acidic form, and the process is performed under acidic pH conditions by the addition of between 0.1 and 0.8 equivalents of an acid based on the amount of aspartic and/or glutamic acid, wherein under the process conditions said cyanide salt reacts with the aspartic acid and/or glutamic acid and the aldehyde, wherein hydrogen cyanide is formed in situ.

2. The process of claim 1, wherein the aldehyde is formaldehyde.

3. The process of claim 1, wherein the amino acid is glutamic acid.

4. The process of claim 1 wherein the reaction of the cyanide, the amino acid and the aldehyde forms a nitrile, and wherein the process contains an additional step wherein the nitrile is hydrolyzed to a carboxylic acid, an amide or a carboxylate salt.

5. The process of claim 1, wherein the pH is between 3 and 6.

6. The process of claim 1, wherein the cyanide salt is an alkali metal cyanide.

7. The process of claim 6, wherein the alkali metal cyanide is sodium cyanide or potassium cyanide.

8. The process of claim 1, wherein the process is carried out in an aqueous solution or an organic protic solvent.

* * * * *